United States Patent
Salciccioli et al.

(10) Patent No.: US 9,695,097 B2
(45) Date of Patent: Jul. 4, 2017

(54) ETHANOL PRODUCTION VIA DIMETHYLETHER RECYCLE

(71) Applicant: ExxonMobil Chemical Patents Inc., Baytown, TX (US)

(72) Inventors: Michael Salciccioli, Houston, TX (US); James H. Beech, Jr., Kingwood, TX (US); Ranjita Ghose, Houston, TX (US); Paul F. Keusenkothen, Houston, TX (US); Meha Rungta, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/185,520

(22) Filed: Jun. 17, 2016

(65) Prior Publication Data
US 2017/0022129 A1 Jan. 26, 2017

Related U.S. Application Data

(60) Provisional application No. 62/194,654, filed on Jul. 20, 2015.

(51) Int. Cl.
| | |
|---|---|
| *C07C 29/00* | (2006.01) |
| *C07C 29/149* | (2006.01) |
| *C07C 29/154* | (2006.01) |
| *C07C 67/37* | (2006.01) |
| *C07C 1/24* | (2006.01) |
| *C07C 1/20* | (2006.01) |
| *B01J 29/24* | (2006.01) |
| *B01J 29/68* | (2006.01) |
| *B01J 23/06* | (2006.01) |
| *B01J 23/72* | (2006.01) |
| *C07C 29/153* | (2006.01) |
| *C07C 41/09* | (2006.01) |

(52) U.S. Cl.
CPC .............. *C07C 29/149* (2013.01); *B01J 23/06* (2013.01); *B01J 23/72* (2013.01); *B01J 29/24* (2013.01); *B01J 29/68* (2013.01); *C07C 1/20* (2013.01); *C07C 1/24* (2013.01); *C07C 29/153* (2013.01); *C07C 29/154* (2013.01); *C07C 41/09* (2013.01); *C07C 67/37* (2013.01); *C07C 2523/06* (2013.01); *C07C 2523/72* (2013.01); *C07C 2529/24* (2013.01); *C07C 2529/68* (2013.01)

(58) Field of Classification Search
CPC ......... C07C 29/24; C07C 29/149; C07C 1/20; C07C 1/124

USPC .......................................................... 568/885
See application file for complete search history.

(56) References Cited

U.S. PATENT DOCUMENTS

| | | |
|---|---|---|
| 2005/0107481 A1 | 5/2005 | Janssen et al. |
| 2007/0259972 A1 | 11/2007 | Lattner et al. |
| 2008/0016833 A1 | 1/2008 | Sheidler et al. |
| 2008/0033218 A1 | 2/2008 | Lattner et al. |
| 2015/0158785 A1 | 6/2015 | Soultanidis et al. |

FOREIGN PATENT DOCUMENTS

| | | |
|---|---|---|
| WO | 2009/077719 | 6/2009 |
| WO | 2009/077720 | 6/2009 |

OTHER PUBLICATIONS

Bhan et al., "*Specificity of Sites within Eight-Membered Ring Zeolite Channels for Carbonylation of Methyls to Acetyls*," Journal of American Chemical Society, 2007, vol. 129, pp. 4919-4924.

Cheung et al., "*Selective Carbonylation of Dimethyl Ether to Methyl Acetate Catalyzed by Acidic Zeolites*," Angewandte Chemie, 2006, vol. 45, pp. 1617-1620.

Li et al., "*Direct Synthesis of Ethanol from Dimethyl Ether and Syngas over Combined H-Mordenite and Cu/ZnO Catalysts*," ChemSusChem, 2010, vol. 3, pp. 1192-1199.

San et al., "*New Synthesis Method of Ethanol from Dimethyl Ether with a Synergic Effect between the Zeolite Catalyst and Metallic Catalyst*" Energy & Fuels, 2009, vol. 23, pp. 2843-2844.

Yang et al., "*A new method of ethanol synthesis from dimethyl ether and syngas in a sequential dual bed reactor with the modified zeolite and Cu/ZnO catalysts*," Catalysis Today, 2011, vol. 164, pp. 425-428.

Gerber et al., "*Mixed Alcohol Synthesis Catalyst Screening*," Pacific Northwest National Laboratory, 2007, PNNL-16763.

*Primary Examiner* — Sikarl Witherspoon

(57) ABSTRACT

This invention relates to a process for producing ethanol comprises supplying a feed comprising carbon monoxide, hydrogen and dimethyl ether to a reaction zone operated under conditions such that (i) part of the carbon monoxide in the feed reacts with part of the hydrogen in the feed to produce methanol; (ii) part of the carbon monoxide in the feed reacts with at least part of the dimethyl ether in the feed to produce methyl acetate; and (iii) part of the hydrogen in the feed reacts with at least part of the methyl acetate produced in (ii) to produce an effluent comprising methanol and ethanol. At least part of the ethanol is recovered from the effluent and at least part of the methanol is dehydrated to produce dimethyl ether, which is recycled to the reaction zone.

19 Claims, 1 Drawing Sheet

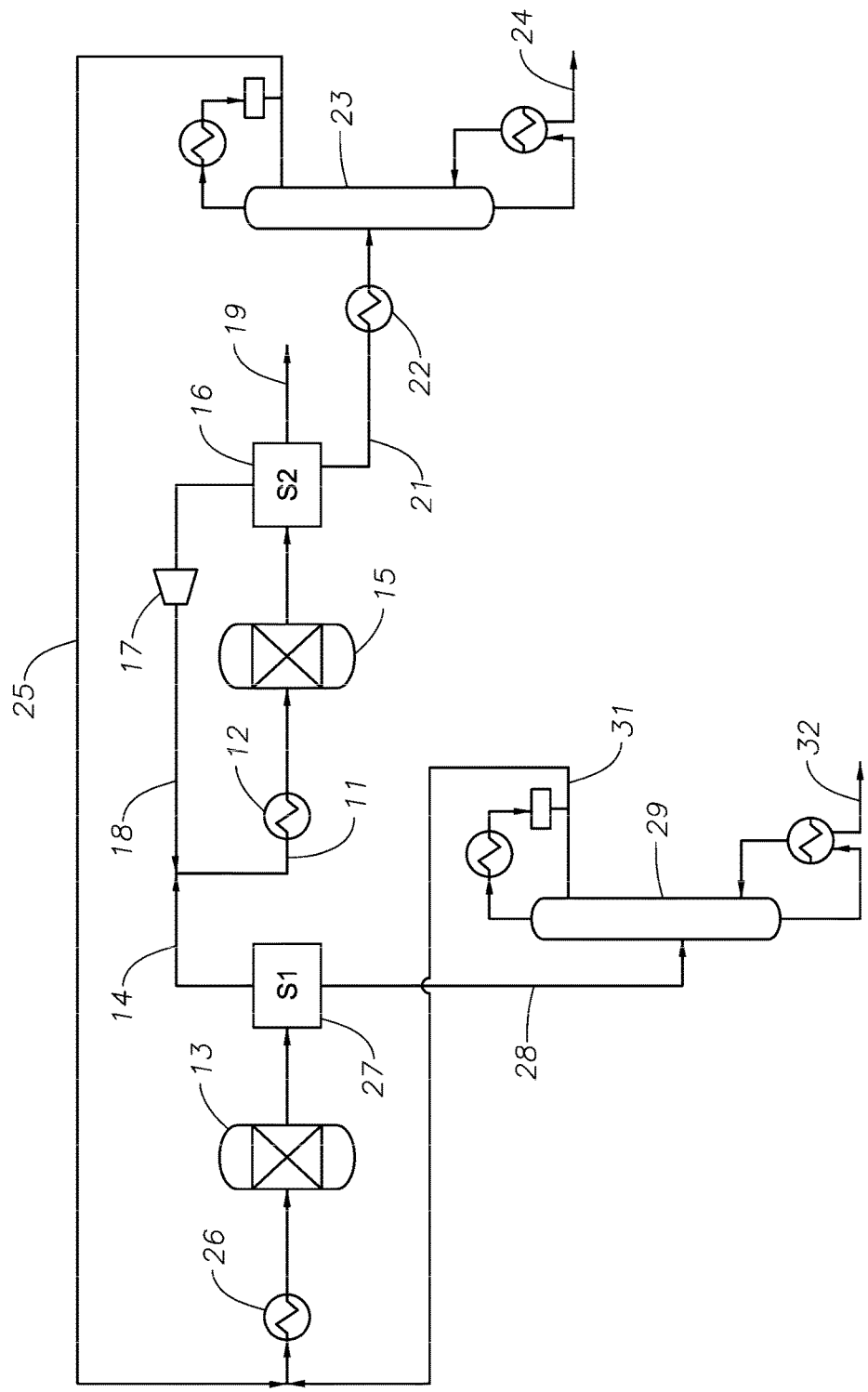

ETHANOL PRODUCTION VIA DIMETHYLETHER RECYCLE

CROSS REFERENCE TO PRIORITY CLAIM

This application claims priority to U.S. Application Ser. No. 62/194,654 filed Jul. 20, 2015, the disclosure of which is fully incorporated herein by reference.

FIELD OF THE INVENTION

This disclosure relates to the production of ethanol and/or ethylene.

BACKGROUND OF THE INVENTION

Ethanol is both a desirable chemical product and feedstock. Ethanol is steadily becoming a promising alternative to gasoline throughout much of the world. Ethanol is also useful for producing ethylene, which is a leading petrochemical in terms of production volume, sales value, and number of derivatives. Ethanol can also be converted to butadiene, a precursor to synthetic rubbers, by the Lebedev process. An economically viable process that can produce ethanol and/or ethylene from methane (or other advantaged carbon-containing feedstock) would therefore be highly desirable. However, existing process schemes that can accomplish this transformation suffer from several drawbacks.

For example, it is known to convert methane directly to ethylene via oxidative coupling, but this route often suffers from low yields (high trade-off between conversion and selectivity), frequently requires expensive oxygen generation facilities, and produces large quantities of undesirable carbon oxides. In addition, non-oxidative methane conversion is equilibrium-limited, and temperatures of 800° C. or more are needed for methane conversions greater than a few percent.

A potentially more attractive route involves converting methane or other carbon-containing feedstock to a mixture comprising carbon monoxide and hydrogen (the mixture being conventionally referred to as "syngas"), converting the syngas to a mixture of oxygenates, and then converting the oxygenates to olefins. See, e.g., US 2005/0107481 A1, US 2008/0033218 A1, and US 2007/0259972 A1, which disclose aspects of converting syngas to a mixture comprising $C_1$ alcohol and $C_2$ alcohol, and then converting the mixture to a product mixture comprising ethylene and propylene. According to those references, approximately 100% of the mixture's ethanol can be selectively converted to ethylene. The mixture's methanol, in contrast, produces (i) ethylene and propylene, in approximately equal amounts, and (ii) a significant amount of by-products. The by-products can include, e.g., one or more of hydrogen, water, alcohols, carboxylic acids, ethers, carbon oxides, ammonia and other nitrogenated compounds, arsines, phosphines, and chlorides. The by-products can also include hydrocarbons, such as one or more of $C_4$ to $C_{30}$ olefins, acetylene, methyl acetylene, propadiene, butadiene, butyne, and the like, and combinations thereof.

Other syngas-based schemes have been proposed which can produce ethylene in higher selectivity, see, for example, San et al. Energy & Fuels 2009, 23, 2843-2844. However, these require the addition of methanol or dimethyl ether co-feeds to satisfy process stoichiometry.

Other references of interest include: Mixed Alcohol Synthesis Catalyst Screening, M. Gerber et al. Pacific Northwest Laboratory 2007, PNNL-16763; US 2015-0158785; Cheung et al. Angew. Chem. Int. Ed. 2006, 45, 1617-1620; Yang et al. Catalysis Today 2011, 164, 425-428; San et al. Energy & Fuels 2009, 23, 2843-2844; WO 2009/077719; Li et al. ChemSusChem 2010, 3, 1192-1199; Bhan et al., J. Am. Chem. Soc. 2007, 129, 4919-4924; and US 2008/016833.

There is, therefore, a need for an efficient process for the conversion of syngas to ethanol (and, if desired, eventually ethylene via ethanol dehydration), which minimizes methanol (or other oxygenates) and/or propylene byproduct production, and also only requires a syngas feed.

SUMMARY OF THE INVENTION

According to the present disclosure, it has now been found that a feed mixture comprising carbon monoxide, hydrogen and dimethyl ether can be directly converted to ethanol in the presence of a single multi-component catalyst system. Methanol is coproduced with the ethanol and can be dehydrated to provide some or all of the dimethyl ether in the feed mixture.

Thus, in one aspect, the present disclosure resides in a process for producing ethanol, the process comprising:
(a) providing a feed comprising carbon monoxide, hydrogen and dimethyl ether;
(b) supplying the feed to at least one reaction zone operated under conditions effective for the following reactions to occur in the at least one reaction zone:
  (i) at least part of the carbon monoxide in the feed reacts with part of the hydrogen in the feed to produce methanol;
  (ii) at least part of the carbon monoxide in the feed reacts with at least part of the dimethyl ether in the feed to produce methyl acetate; and
  (iii) at least part of the hydrogen in the feed reacts with at least part of the methyl acetate produced in (ii) to produce methanol and ethanol;
(c) removing an effluent comprising ethanol and methanol from the at least one reaction zone;
(d) recovering at least part of the ethanol from the effluent;
(e) dehydrating at least part of the methanol in the effluent to produce dimethyl ether; and
(f) recycling at least part of the dimethyl ether produced in (e) to the feed (a). In one embodiment, the process further comprises:
(g) dehydrating at least part of the ethanol recovered in (d) to produce ethylene. In another embodiment, the process further comprises:
(h) converting at least part of the ethanol recovered in (d) to butadiene.

BRIEF DESCRIPTION OF THE DRAWINGS

FIG. 1 is a flow diagram of a process for producing ethanol and optionally ethylene by a process according to one embodiment of the present disclosure.

DETAILED DESCRIPTION OF THE EMBODIMENTS

As used herein, the numbering scheme for the groups of the Periodic Table of the Elements is the New numbering as disclosed in Chemical and Engineering News, 63(5), 27 (1985).

A process is described for the direct conversion of a feed mixture comprising at least carbon monoxide and hydrogen, such as synthesis gas, to ethanol via a dimethyl ether (DME) carrier. The process comprises the following reactions:

1. Reaction of carbon monoxide with hydrogen in the feed mixture to produce methanol. This reaction may be summarized as follows:

$$2H_2+CO \rightarrow CH_3OH$$

2. Dehydration of methanol to produce dimethyl ether (DME). This reaction may be summarized as follows:

$$2CH_3OH \rightarrow CH_3OCH_3+H_2O$$

3. Carbonylation of dimethyl ether (DME) with carbon monoxide from the synthesis gas to produce methyl acetate. This reaction may be summarized as follows:

$$CH_3OCH_3+CO \rightarrow CH_3COOCH_3$$

4. Hydrogenation of methyl acetate to produce methanol and ethanol. This reaction may be summarized as follows:

$$CH_3COOCH_3+2H_2 \rightarrow C_2H_5OH+CH_3OH$$

In the present process the methanol synthesis reaction (1), the DME carbonylation reaction (3) and the methyl acetate hydrogenation reaction (4) are carried out in the same first reaction zone or reaction zones to produce a reaction effluent comprising ethanol and methanol. At least part of the ethanol is recovered from the reaction effluent, while at least part of the methanol in the effluent is dehydrated to produce dimethyl ether according to reaction (2), typically in a second reaction zone or zones separate from the first reaction zone(s). Part or all of the resultant dimethyl ether can then be recycled to the first reaction zone(s). It will be seen that, if the reaction conditions in the first reaction zone(s) are controlled so that the molar ratio of methanol to ethanol in the effluent from the first reaction zone(s) is maintained at approximately 2:1, then (assuming ideal conversion and selectivity in the methanol dehydration step) methanol does not have to be purchased for the process, significant excess methanol will not be generated by the process and the only recovered product will be ethanol. If the resultant ethanol is then dehydrated to produce ethylene, the only significant by-product will be water.

Production of Carbon Monoxide-Hydrogen Mixture

The mixture of carbon monoxide and hydrogen used as the feed in the present process can be produced from methane and/or other carbon-containing source materials. The type of carbon-containing source material used is not critical. For example, the source material can comprise methane and other lower ($C_4$—) alkanes, such as contained in a natural gas stream, or can comprise heavier hydrocarbonaceous materials, such as coal and biomass. Desirably, the carbon-containing source material comprises ≥10 vol. %, such as ≥50 vol. %, based on the volume of the source material, of at least one hydrocarbon, especially methane.

The source material is initially converted to a carbon monoxide-hydrogen mixture by any convenient method, including those well-established in the art. Suitable methods include those described in US 2007/0259972 A1, US 2008/0033218 A1, and US 2005/0107481, each of which is incorporated by reference herein in its entirety. Certain aspects where the carbon monoxide-hydrogen (i.e., molecular hydrogen) mixture is synthesis gas, also abbreviated to syngas, will now be described in more detail. The invention is not limited to these aspects, and this description is not meant to foreclose other aspects within the broader scope of the invention, such as those where the carbon monoxide-hydrogen mixture does not contain syngas.

Natural gas can be converted to syngas by steam reforming. The first step normally involves the removal of inert components in the natural gas, such as nitrogen, argon, and carbon dioxide. Natural gas liquids will also be recovered and directed to other processing or transport. The treated natural gas will comprise primarily methane and some ethane with small amounts of higher alkanes, such as propane. Preferably, the natural gas comprises more than 90 vol. % methane. The treated natural gas is then contacted with steam in the presence of a catalyst, such as one or more metals or compounds thereof selected from Groups 7 to 10 of the Periodic Table of the Elements supported on an attrition resistant refractory support, such as alumina. The contacting is normally conducted at high temperature, such as in the range of from 800° C. to 1100° C., and pressures ≤5000 kPa. Under these conditions, methane converts to carbon monoxide and hydrogen according to reactions, such as:

$$CH_4+H_2O=CO+3H_2.$$

A second method is partial oxidation, in which the methane is burned in an oxygen-lean environment. The methane is partially-oxidized to carbon monoxide (reaction (i)), with a portion of the carbon monoxide being exposed to steam re-forming conditions (reaction (ii)) to produce hydrogen and carbon dioxide, according to the following representative reactions:

$$CH_4+3/2O_2=CO+2H_2O \qquad (i),$$

$$CO+H_2O=CO_2+H_2 \qquad (ii).$$

Partial oxidation is exothermic and yields a significant amount of heat. Because one reaction is endothermic and the other is exothermic, steam reforming and partial oxidation are often performed together for efficient energy usage. Combining the steam reforming and partial oxidation yields a third process wherein the heat generated by the partial oxidation is used to drive the steam reforming to yield syngas.

Another route for producing syngas is autothermal reforming (ATR) which uses a mixture of oxygen and carbon dioxide or steam to convert methane to form syngas. The reaction takes place in a single chamber where the methane is partially oxidized. The reaction is exothermic due to the oxidation. When the ATR uses carbon dioxide the $H_2$:CO ratio produced is 1:1; when the ATR uses steam the $H_2$:CO ratio produced is 2.5:1. The reactions may be summarized as follows:

$$2CH_4+O_2+CO_2=3CO+3H_2+H_2O$$

$$4CH_4+O_2+2H_2O=10H_2+4CO$$

Whatever the source of the mixture of carbon monoxide and hydrogen used in the present process, in certain embodiments the mixture may comprise a $H_2$:CO molar ratio in the range of from 0.5 to 20, or 0.5 to 10, or 0.5 to 4, preferably about 1 to 2.5. In addition, the mixture may contain other components, such as carbon dioxide, in which case the ($H_2$—$CO_2$):(CO+$CO_2$) ratio of the mixture may desirably be in the range from 0.1 to 20, such as from 1 to 2.5.

Conversion of Carbon Monoxide-Hydrogen Mixture to Ethanol

In the present process conversion of the feed mixture of carbon monoxide and hydrogen to ethanol is effected in a single reactor or a series of reactors each containing a multi-component catalyst system effective to promote the methanol synthesis reaction (1), the DME carbonylation reaction (3) and the methyl acetate hydrogenation reaction (4) described above. In addition, the reactor(s) receive a supply of dimethyl ether (DME) produced by dehydration of at least part of the methanol co-produced with ethanol in the methyl acetate hydrogenation reaction (4). In some embodiments, the supply of DME to the reactor is such that the molar ratio of CO:DME in the total feed is from 1 to 100, such as from 1 to 10.

The multi-component catalyst system may comprise a first catalyst comprising at least one molecular sieve and a second catalyst comprising at least one metal oxide. The first and second catalysts may be contained in separate catalyst beds arranged, for example, in a stacked bed configuration or may be mixed together in a single catalyst bed.

In some embodiments, the first catalyst may comprise at least one molecular sieve preferably selected from mordenite and/or ferrierite (preferably the proton form of mordenite (H-MOR) and/or ferrierite (H-FER)), or any molecular sieve material with 8-member ring (8-MR) channels or 8-MR pockets such as chabazite, dachiardite, natrolite, offretite, wenkite, and/or SAPO-40. In addition, the first catalyst may contain a hydrogenation component, such as a metal selected from Groups 3 to 13 of the Periodic Table of the Elements. The hydrogenation component can comprise one or more neutral metals selected from Groups 3 to 13 of the Periodic Table of the Elements, such as Ga, In, Zn, Cu, Re, Mo, W, La, Fe, Ag, Pt, Pd, and/or one or more oxides, sulfides, nitrides, and/or carbides of these metals. For example, a suitable hydrogenation metal is copper or an oxide form of copper. The hydrogenation component can be provided on the catalyst in any manner, for example, by conventional methods such as impregnation or ion exchange of the molecular sieve with a solution of a compound of the relevant metal, followed by conversion of the metal compound to the desired form, namely neutral metal, oxide, sulfide, and/or carbide. Part or all of the hydrogenation metal may also be present in the crystalline framework of the molecular sieve. In some embodiments, the hydrogenation component is typically present in an amount of at least 0.1 wt %, such as from 0.1 to 10 wt % of the total catalyst weight.

In addition to the molecular sieve component and, optional, hydrogenation component, the first catalyst may be composited with another material which is resistant to the temperatures and other conditions employed in the conversion reaction. Such materials include active and inactive materials and synthetic or naturally occurring zeolites, as well as inorganic materials such as clays and/or oxides such as alumina, silica, silica-alumina, zirconia, titania, magnesia or mixtures of these, and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The second catalyst is different from the first catalyst and comprises at least one metal oxide, usually zinc oxide, either alone or in combination with copper and/or copper oxide, iron and/or iron oxide, nickel and/or nickel oxide, titanium and/or titanium oxide, silica, alumina and one or more optional promoters (in metal or oxide form), such as chromia and alumina, and/or additional promoters such as sodium, calcium, potassium, caesium, and/or magnesium. In one embodiment, the second catalyst comprises from 1 to 70 wt % zinc oxide and from 30 to 99 wt % copper and/or copper oxide, based upon the weight of the catalyst. The second catalyst may also comprise a refractory support, such as silica, silca-alumina or alumina.

In some embodiments, the weight ratio of the first catalyst to the second catalyst in the first reaction zone(s) is from 0.01 to 100, such as from 0.1 to 10.

The conditions in the reaction zone(s) used to convert the carbon monoxide, hydrogen and dimethyl ether feed to ethanol and methanol can vary widely, but in some embodiments include a temperature from 100° C. to 400° C., such as from 200° C. to 300° C. and a pressure from 500 kPa-a to 15,000 kPa-a, such as from 3,000 kPa-a to 10,000 kPa-a. The conditions may be controlled so as to effect near complete conversion of the dimethyl ether and the methyl acetate intermediate so that the effluent from the reaction zone(s) is composed mainly of ethanol and methanol, together with unreacted carbon monoxide and hydrogen. In some embodiments, the molar ratio of methanol to ethanol in the effluent is from 1:1 to 10:1, preferably from 1.5 to 5:1, preferably about 2:1 to about 4:2. Alternately the molar ratio of methanol to ethanol in the effluent is at least 2:1.

The combined reactions (1), (3), and (4) are exothermic and in some embodiments may be conducted in one or more tubular reactors with heat removal to allow isothermal operation.

The effluent produced from reactions (1), (3), and (4) is initially fed to a separator for removal of the unreacted gaseous components, which can then be recycled back to the reaction zone(s). The remainder of the effluent is then supplied an alcohol splitter where the methanol is removed as an overhead stream and is supplied to the dehydration reaction (2). The ethanol is recovered as a bottoms stream and can either be sold as-is or converted to ethylene and/or butadiene as described below.

Methanol Dehydration

Methanol dehydration to produce dimethyl ether is a well known reaction and any conventional method of conducting this reaction can be used in the present process. For example, dimethyl ether is commonly produced by the Lewis or Bronsted acid catalysed dehydration of methanol, for which known catalysts include iron chloride, copper sulphate, copper chloride, manganese chloride, aluminum chloride, aluminum sulphate, chromium sulphate, alums, thorium compounds, aluminum oxide, titanium oxide, barium oxide, silica gel aluminum phosphate, and acidic ionic liquids. Preferred dehydration catalysts are heterogeneous catalysts, such as aluminum oxides and aluminum silicate, which can be modified by doping. Zeolites, such as ZSM-5, strong acid ion exchange resins and supported heteropolyacids (such as silicotungstenic acid) can also be advantageously used as dehydration catalysts. Suitable conditions for the dehydration process include a temperature of about 250° C. to about 700° C., and preferably about 350° C. to 500° C.; a weight hourly space velocity (WHSV) of about 0.5 to 50, preferably about 1.0 to 10.0, and at an absolute pressure of about 0.2 to 30 atmospheres.

The dehydration reaction is exothermic and in some embodiments may be conducted in one or more tubular reactors with heat removal to allow isothermal operation.

During the methanol dehydration process to produce dimethyl ether, water is also produced. Some or all of the water may be removed from etherification effluent before the dimethyl ether is supplied to the first reaction zone(s). Desirably, substantially all of the dimethyl ether required for the carbonylation reaction (3) is produced by dehydration of the methanol coproduced in the hydrogenation reaction (4). In this way, the need for a separate supply of fresh dimethyl ether can be obviated or reduced. Alternately, at least 10 wt % (preferably from 10 to 100 wt %, preferably from 40 to 95 wt %, preferably from 75 to 90 wt %) of the DME provided for the carbonylation reaction (3) is produced by dehydration of the methanol co-produced in the hydrogenation reaction (4).

Conversion of Ethanol to Ethylene and/or Butadiene

In some embodiments, the ethanol produced by the present process is further converted to ethylene and/or butadiene. It is known that ethanol can be dehydrated to produce ethylene according to the following reaction:

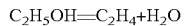

The reaction is conveniently conducted in the presence of an acid catalyst, such as sulfuric acid or, more preferably a heterogeneous catalyst, such as alumina, or silica-alumina, zeolites. The reaction may be conducted at a temperature of 300° C. to 550° C.

In addition, ethanol can be converted to butadiene via the Lebedev reaction which may be summarized as follows:

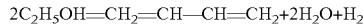

The reaction may be conducted at 400-450° C. over any of a variety of metal oxide catalysts, such as alumina.

Referring now to FIG. 1, a flow diagram is shown of a process for producing ethanol and, optionally, ethylene from synthesis gas according to one embodiment of the present disclosure. In this embodiment, a syngas feed (fresh and/or recycled) is supplied via line 11 to a heat exchanger 12, which also receives a supply of dimethyl ether (DME) from a methanol dehydration unit 13 via line 14. The heat exchanger 12 heats the syngas/DME mixture and supplies the heated mixture to a reactor 15 containing a bed of a first molecular sieve catalyst, such as Cu/H-mordenite, stacked on a bed of a second metal oxide catalyst, such as Cu/ZnO. The conditions in the reactor 15 are maintained such that the reactions (1), (3), and (4) occur to produce an effluent comprising ethanol, methanol, and unreacted CO and hydrogen.

The effluent from the reactor 15 is supplied to a separator 16, such as a distillation column, where at least part of the unreacted CO and hydrogen is removed, compressed in compressor 17 and recycled via line 18 back to the heat exchanger 12 and reactor 15. A further part of the unreacted CO and hydrogen, or other inert gases or reaction byproducts, may be purged via line 19. After removal of the unreacted CO and hydrogen, the remainder of the effluent is fed via line 21 to a cooler 22 and then to an alcohol splitter tower 23, which separates the ethanol and methanol in the effluent. The ethanol is collected as a bottoms stream, which typically contains at least 99 wt % of the ethanol in the effluent and which is recovered via line 24 for optional conversion to ethylene and/or butadiene. The methanol exits the tower 23 as an overhead stream and is fed via line 25 to a heat exchanger 26 (where a methanol purge (not shown) may be incorporated in case more methanol is produced than can be converted by the methanol dehydration unit 13), where the methanol is heated before being fed to the methanol dehydration unit 13.

The methanol dehydration unit 13 contains a catalyst, such as ZSM-5, and is operated under conditions that the methanol is dehydrated to produce an effluent composed of dimethyl ether and water, together normally with some unreacted methanol. The effluent from the methanol dehydration unit 13 is supplied to separator 27, such as a flash drum, where the dimethyl ether is recovered for supply to the reactor 15 and the water and unreacted methanol are collected and fed via line 28 to a methanol recovery tower 29. The methanol recovery tower 29 is operated such that the unreacted methanol exits the tower as overhead stream 31, while the water is collected as bottoms stream 32. The methanol-containing overhead stream 31 is then recycled to the dehydration unit 13 via heat exchanger 26.

The invention will now be more particularly described with reference to the following non-limiting Example.

Example

A simulation of the process shown in FIG. 1 is conducted in which 300 lbmole/hr of fresh CO and 500 lbmole/hr of fresh hydrogen are supplied to the reactor 15 via line 11, while 100 lbmole/hr of DME from recycled methanol are supplied to the reactor 15 via line 14. The reactor 14 also receives 3000 lbmole/hr of recycled CO and 3000 lbmole/hr of recycled hydrogen via line 25. Thus, at the inlet to the reactor 15, the CO/DME ratio is about 33:1 and the CO/H$_2$ ratio is about 1:1.

The reactor 15 is operated isothermally at a temperature of 427° F. (219° C.) and a pressure of 217 psia (1496 kPa-a) and, assuming 100% conversion of the DME and methyl acetate, produces 200 lbmole/hr of methanol and 100 lbmole/hr of ethanol.

The methanol dehydration unit 13 receives 200 lbmole/hr of methanol recycled via line 25 and 22.2 lbmole/hr of methanol recycled via line 31. The unit 13 is operated isothermally at a temperature of 355° F. (179° C.) and a pressure of 217 psia (1496 kPa-a) and, assuming 90% conversion of the methanol, produces about 100 lbmole/hr of DME.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

All documents described herein are incorporated by reference herein, including any priority documents and/or testing procedures to the extent they are not inconsistent with this text. Further, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for producing ethanol, the process comprising:
   (a) providing a feed comprising carbon monoxide, hydrogen and dimethyl ether;
   (b) supplying the feed to at least one reaction zone operated under conditions effective for the following reactions to occur in the at least one reaction zone:
      (i) at least part of the carbon monoxide in the feed reacts with part of the hydrogen in the feed to produce methanol;
      (ii) at least part of the carbon monoxide in the feed reacts with at least part of the dimethyl ether in the feed to produce methyl acetate; and
      (iii) at least part of the hydrogen in the feed reacts with at least part of the methyl acetate produced in (ii) to produce methanol and ethanol,
      wherein the reaction zone comprises a first catalyst comprising mordenite and/or ferrierite and a second catalyst comprising at least one metal oxide, wherein the first catalyst further comprises a hydrogenation metal, and wherein the first and second catalysts are contained in separate catalyst beds;
   (c) removing an effluent comprising ethanol and methanol from the at least one reaction zone, wherein the molar ratio of methanol to ethanol in the effluent is at least 2:1;
   (d) recovering at least part of the ethanol from the effluent;
   (e) dehydrating at least part of the methanol in the effluent to produce dimethyl ether; and
   (f) recycling at least part of the dimethyl ether produced in (e) to the feed (a).

2. The process of claim 1, wherein the first catalyst further comprises copper.

3. The process of claim 1, wherein the second catalyst comprises zinc oxide.

4. The process of claim 3, wherein the second catalyst further comprises copper and/or copper oxide.

5. The process of claim 1, wherein the conditions in the reaction zone include a temperature from 100° C. to 400° C.

6. The process of claim 1, wherein the conditions in the reaction zone include a pressure from 500 kPa-a to 15,000 kPa-a.

7. The process of claim 1, wherein the molar ratio of carbon monoxide to dimethyl ether in the feed is from 1 to 100.

8. The process of claim 1, wherein the molar ratio of hydrogen to carbon monoxide in the feed is from 0.05 to 4.

9. The process of claim 1, wherein substantially all of the dimethyl ether in the feed is produced by the dehydrating (e).

10. The process of claim 1, wherein the molar ratio of methanol to ethanol in the effluent is from 1:1 to 10:1.

11. The process of claim 1, wherein at least part of the carbon monoxide and hydrogen in the feed comprises syngas.

12. The process of claim 11, wherein at least part of the syngas is produced by oxidation of a carbon-containing material.

13. The process of claim 12, wherein the carbon-containing material comprises methane.

14. The process of claim 11, wherein at least part of the syngas is produced by reaction of a hydrocarbon with water.

15. The process of claim 1 further comprising:
   (g) dehydrating at least part of the ethanol recovered in (d) to produce ethylene.

16. The process of claim 1 further comprising:
   (h) converting at least part of the ethanol recovered in (d) to produce butadiene.

17. The process of claim 1, wherein the first and second catalysts are contained in separate stacked catalyst beds.

18. The process of claim 1, wherein the weight ratio of the first catalyst to the second catalyst in the reaction zone is from 0.1 to 10.

19. The process of claim 7, wherein the molar ratio of carbon monoxide to dimethyl ether in the feed is from 1 to 10.

* * * * *